United States Patent [19]
Grenier et al.

[11] Patent Number: 5,338,684
[45] Date of Patent: Aug. 16, 1994

[54] STABLE AQUEOUS FK506 STANDARDS

[75] Inventors: Frank C. Grenier, Libertyville; Julie A. Luczkiw, Addison; Merry E. Bergmann, Lombard, all of Ill.; David R. Blonski, Kenosha, Wis.

[73] Assignee: Abbott Laboratories, Abbott Park, Ill.

[21] Appl. No.: 71,942

[22] Filed: Jun. 2, 1993

Related U.S. Application Data

[63] Continuation of Ser. No. 752,410, Aug. 30, 1991, abandoned.

[51] Int. Cl.$^5$ ............................................. G01N 31/00
[52] U.S. Cl. ......................................... 436/8; 436/10; 436/17; 436/18
[58] Field of Search ................ 436/8, 10, 11, 17, 18

[56] References Cited

U.S. PATENT DOCUMENTS

| | | | |
|---|---|---|---|
| 4,250,051 | 2/1981 | Armstrong | 436/17 |
| 4,324,687 | 4/1982 | Louderback et al. | 435/2 |
| 4,731,330 | 3/1988 | Hill et al. | 436/18 |
| 4,777,139 | 10/1988 | Wong et al. | 436/18 |
| 4,945,062 | 7/1990 | Chiang | 436/11 |
| 5,023,186 | 6/1991 | Herring | 436/8 |
| 5,109,112 | 4/1992 | Siekierka et al. | 435/233 |
| 5,116,756 | 5/1992 | Dumont et al. | 435/886 |
| 5,164,495 | 11/1992 | Lunetta | 540/456 |

FOREIGN PATENT DOCUMENTS 30293892 12/1988 European Pat. Off. .

OTHER PUBLICATIONS

Christians, et al., *Specific and Sensitive Measurement of FK506 and Its Metabolites Blood and Urine of Liver-Graft Recipients,* Clin. Chem. 38/10, pp. 2025-2032 (1992).

Murthy, et al., *Radioreceptor Assay for Quantifying FK-506 Immunosuppressant in Whole Blood,* Clin. Chem. 38/7, pp. 1307-1310 (1992).

*Primary Examiner*—James C. Housel
*Assistant Examiner*—Lien Tran
*Attorney, Agent, or Firm*—Gregory W. Steele

[57] ABSTRACT

A stabilized, aqueous composition containing FK506. FK506 degrades rapidly in most aqueous matrices. The rate of degradation is decreased in the presence of unfixed blood cells or fragments of blood cells from human or animal sources. A number of matrices using blood components are possible. Blood can be used directly or the blood cells can be lysed. The blood is diluted with a solution of an alkali halide.

21 Claims, No Drawings

STABLE AQUEOUS FK506 STANDARDS

This application is a continuation of U.S. patent application Ser. No. 752,410 filed Aug. 30, 1991 now abandoned.

BACKGROUND OF THE INVENTION

1. Technical Field

The present invention is directed to an in vitro aqueous composition of the drug, FK506 having enhanced stability. The invention utilizes blood cells or fragments of blood cells to stabilize the drug in an aqueous matrix, preferably an aqueous matrix also containing an alkali halide.

2. Background

FK506 is an immunosuppressant useful for the treatment of rejection following transplant surgery, graft versus host disease and autoimmune diseases in humans. FK506 corresponds to the following structural formula, (I):

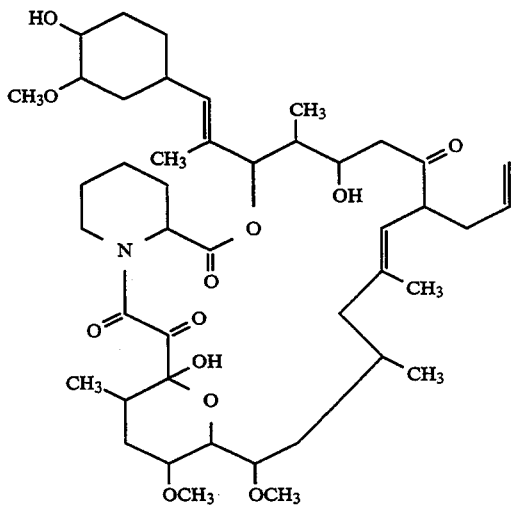

FK506 is a macrolide antibiotic isolated from the fungus *Streptomyces tsukubaensis* by the Fujisawa Pharmaceutical Company of Japan. Cyclosporine, another immunosuppressant (but having a totally different structure from FK506), has also been used to control rejection. During cyclosporine therapy, monitoring the blood concentration of cyclosporine is an important aspect of clinical care. Accordingly, it is expected that monitoring blood concentrations of FK506 will be important for patients receiving this drug.

To accurately and precisely measure blood concentrations of FK506, an appropriate analytical method must be available. Typically, many analytical methods require utilization of a standard composition of the analyte to be measured, often as an essentially aqueous composition. However, FK506 tends to degrade rapidly in aqueous matrices. Accordingly, there is a need for stable aqueous compositions of FK506 for utilization, for example, as aqueous standards for diagnostic assays for FK506.

EP 0 293 892 A2 describes an ELISA methodology to measure FK506 comprised of 1) an ELISA plate coated with anti-FK506 antibodies, 2) an FK506-horseradish peroxidase conjugate which competes with free FK506 and acts as a signal generating reagent and 3) an appropriate substrate for the peroxidase. While the ELISA assay is effective, it is subject to improvement. Automated or semi-automated immunological technologies are typically both more precise and accurate and have greater throughput than ELISA formats. The Abbott IMx® analyzer is one such system which can run, for example, microparticle capture enzyme immunoassays (MEIAs). A number of serum-based assays have been developed for the IMx® but thus far no whole blood tests have been developed which are compatible with the MEIA format. Moreover, the need for providing an aqueous composition of FK506 of enhanced stability has been a challenge in the development of a diagnostic assay for FK506 which uses whole blood. A semi-automated whole blood assay for FK506 is described herein which provides a much needed and reliable means of measuring blood FK506 concentrations in patient samples and which utilizes, as a standard, a stabilized aqueous matrix containing FK506.

SUMMARY OF THE INVENTION

The invention provides for a stabilized aqueous matrix containing FK506. A stable aqueous matrix containing FK506 can have different applications. However, it is contemplated that a stable aqueous matrix containing FK506 is most useful as a standard for utilization in diagnostic assays. Immunological methods require relatively stable aqueous drug standards in order to accurately extrapolate drug concentrations in patient samples from a calibration curve. The quality control schemes of most assay systems are also predicated on using stable drug standards to assess assay reliability. More stable standards also minimize the opportunity for error incurred from having to make standards frequently.

FK506 has been found to be inherently unstable in aqueous matrices. Serum, plasma and synthetic matrices containing FK506 have all been found to be unstable. Applicants have found that blood components, either human or animal, can increase the stability of FK506 to acceptable levels to provide aqueous FK506-containing compositions of enhanced stability for diagnostic purposes. Unmodified whole blood of human or animal origin has been observed to be useable in the invention, but modification of the blood is preferred. Blood components can be modified by lysis of blood cells, adjustment of blood pH, removal of plasma components and dilution in saline solution to change the normal blood protein concentrations and hematocrit.

Accordingly, the present invention provides for an in vitro aqueous composition suitable as a standard for a diagnostic assay for FK506. A composition of the invention comprises: FK506, whole blood cells or a whole blood component consisting essentially of whole blood cells which have been lysed, water, an organic solvent compatible with FK506, and optionally an alkali halide such as sodium chloride and/or potassium chloride. Preferred compositions of the invention contain alkali halide.

DETAILED DESCRIPTION OF THE INVENTION

A composition (or matrix) of the invention comprises, and preferably consists essentially of: the drug FK506, whole blood cells or a whole blood component consisting essentially of whole blood cells which have been lysed, water, an organic solvent compatible with FK506, and preferably an alkali halide such as sodium chloride and/or potassium chloride. The blood cells, or whole blood component from lysed blood cells, are present in a composition of the invention in an amount sufficient to effectively enhance the stability of the resultant composition over the stability of the same composition but without the presence of the blood cells lysed or unlysed. Preferred compositions of the invention are isotonic at a temperature of 20 degrees Celsius and a pressure of 1 atmosphere.

All compositions (matrices) of the invention involve the use of blood or blood components (fragments) to stabilize FK506. The simplest matrix requires that FK506 is added directly to whole blood to which an anti-coagulant such as ethylene diamine tetraacetic acid (EDTA) typically has been added. The blood can be of human or animal origin. For example, blood from sheep, cows, or horses may be utilized for preparation of a composition of the invention.

A number of modifications to this basic matrix can be made as necessary for specific applications. Whole blood suffers from the disadvantage that blood cells settle resulting in a non-homogeneous matrix. This can be minimized by lysing the blood cells into cell fragments which settle much less rapidly. Cell lysis can be achieved in a number of ways including, for example, repetitive freeze-thaw cycles, dilution with non-isotonic solutions, sonication, heating, addition of detergents and the use of specific lysis agents.

The basic matrix can also be modified by dilution with a solution of an alkali halide such as sodium chloride (saline solution) and/or potassium chloride or other solutions with or without cell lysis. Compositions of the invention containing an alkali halide are preferred. Hence, normal concentrations of blood components can thus be modified somewhat and the matrix will still confer increased stability to FK506.

In some cases, packed red blood cells may be available (for example from blood collection agencies) and a matrix can be configured starting from these cells. The cells can be diluted with many solutions including saline, serum or plasma. If isotonic solutions are used, the cells can subsequently be lysed if desired. Non-isotonic solutions can be used for dilution and simultaneous lysis of packed red blood cells.

The preferred matrix is lysed blood which has been diluted with an aqueous solution of alkali halide such as saline to help minimize the thickening of blood at elevated temperatures which may occur, for example, in automated or semi-automated diagnostic instruments or as a result of shipping or handling. Thickened blood has, for example, the disadvantage of being difficult or impossible to pipette. Dilution also lowers the cost of the matrix by replacing a portion of the expensive whole blood with much less expensive alkali halide solution. Preferably a saline solution containing 0.9 percent by weight sodium chloride is utilized for the purpose of dilution with an alkali halide solution.

Typically compositions of the invention suitable for use as standards for diagnostic assays are made by mixing (diluting) a stock standard of FK506 into one of the matrices described herein. Typically a stock solution of FK506 in anhydrous methanol is used as a starting reagent for preparation of a composition of the invention. For many purposes it is preferred that the organic solvent content of the final aqueous composition be minimized. The organic solvent typically utilized in a composition of the invention is methanol. However, other organic solvents (or diluents) may be employed where desired, examples of which include: ethanol, chloroform, dimethyl formamide (DMSO) and the like. The organic solvent content of a composition of the invention generally is less than 10 percent (weight/volume), more preferably less than 5 percent, and most preferably less than 1 percent, based on the total volume of the final composition. Typically, the limiting factor on the upper amount of organic solvent or diluent that can be employed is undesirable precipitation or coagulation of the blood when too much organic solvent or diluent is present.

An aqueous composition of the invention suitable for use as a standard for a diagnostic assay typically has a hematocrit, based on whole blood cells, of less than 40 percent by volume of the total composition, and preferably has a hematocrit of about 35 percent. As used herein, the hematocrit is the percentage of blood cells in a blood-containing composition as determined by centrifuging blood in a "hematocrit tube" until the cells become packed tightly in the bottom of the tube. Because it is impossible for the blood cells to be compacted completely when measuring hematocrit, a small percentage of plasma remains entrapped among the cells. A true hematocrit averages about 96 percent of the measured hematocrit. As used herein, hematocrit refers to the measured hematocrit. It is also to be understood that for compositions of the invention wherein the blood cells have been lysed, the hematocrit of the composition refers to the measured hematocrit based on whole blood cells. Accordingly, in the preparation of such compositions of the invention, the hematocrit of the whole blood is measured before lysing, and any dilutions performed after cell lysis which are referenced back to hematocrit, are referenced back to the hematocrit as measured before cell lysis. It is also to be understood that the phrase "whole blood component consisting essentially of whole blood cells having been lysed so as to be essentially free of microscopically visible blood cells" is intended to refer to that fraction of whole blood composed of blood cells (i.e., hematocrit) which has been lysed to an extent that whole blood cells are not visible upon inspection with a light microscope.

While the amount of FK506 in a composition of the invention is limited only by its solubility and by the intended use of the composition, preferred compositions of the invention contain from 5 to 70 nanograms FK506/milliliter (ml) based on the total volume of the composition, more preferably from 10 to 60 nanograms FK506/ml for use as a standard (or calibrator) for a semi-automated, microparticle capture enzyme immunoassay for FK506 run on the IMx ® analyzer available from Abbott Laboratories.

It has also been found that the stability of FK506 in aqueous compositions is enhanced somewhat at acidic pH, i.e., at a pH of less than 7. While the stability effect increases moving toward more acidic pH, the ultimate level of acidity is also determined by the intended use of the composition. For preferred embodiments of the invention where the composition of the invention is utilized as a standard or calibrator for a semi-automated FK506 assay, a pH of from 6.0 to 6.5 is preferred. The pH of a composition of the invention can be adjusted by the addition of any pH-lowering material which is compatible with the components of the composition. In the illustrative examples herein, 3 Molar citric acid is utilized to adjust the pH of a composition of the invention.

Although it is to be understood that the order in which the components of a composition of the invention can be brought together may vary, the following procedure has been utilized to prepare preferred compositions of the invention. Whole blood is obtained and its hematocrit is determined. Where desired, the whole blood utilized can contain an anti-coagulant such as the sodium salt of ethylene diamine tetraacetic acid (EDTA), heparin, oxalic acid, citric acid, sodium fluoride and the like. EDTA is a preferred anti-coagulant in preferred compositions of the invention. Next antimicrobial agents such as sodium azide (e.g., to a final concentration of about 0.1% w/v), sodium alkyl paraben (e.g., about 0.1% w/v), and quinolone (e.g., about 0.0005% w/v)are added to the composition. It should be understood that the antimicrobial agents are optional in a composition of the invention. Next the blood cells are lysed (i.e., broken down into fragments) using well known techniques such as subjecting the blood to freeze/thaw cycles (typically about 3 cycles) or to sonication until whole blood cells are no longer visible using a light microscope. Next, the composition is diluted with an aqueous solution of alkali halide such as a 0.9 percent by weight aqueous solution of sodium chloride (saline) to a final, calculated hematocrit of less than 40 percent, typically about 36 percent. Antimicrobial agents also may be employed in the aqueous solution of alkali halide where desired, and typically are so employed in preferred embodiments of the invention. Thereafter, the pH of the resulting composition is adjusted to a value of less than 7.0, typically to a pH of from 6.0 to 6.4, using an acid such as 3 Molar citric acid.

In preparing a composition of the invention, generally from 90 to 20 percent by volume whole blood to 10 to 80 percent by volume aqueous alkali halide solution, preferably from 90 to 70 percent whole blood to 10 to 30 percent alkali halide solution, and most preferably from 90 to 80 percent whole blood to 10 to 20 percent alkali halide solution, is utilized.

Preferred compositions of the invention are isotonic at 20 degrees Celsius and 1 atmosphere pressure.

Compositions of the invention have been found to have an advantageous degree of stability. The stability of the composition can be determined by measuring the decrease in the measured amount of FK506 in the aqueous composition with time. FK506 in a composition of the invention utilizing whole blood cells or blood cell fragments (following lysing) exhibits enhanced stability over an aqueous composition of FK506 which does not contain whole blood cells or blood cell fragments. In a composition of the invention useful as a standard for a diagnostic assay, generally the amount of FK506 initially present in the aqueous composition maintained at a temperature of 37 degrees Celsius will decrease over a period of 7 days by less than 20 percent by weight, and typically by less than 5 percent by weight Compositions of the invention have been found to be particularly useful as standards for a microparticle capture enzyme immunoassay (MEIA) for FK506 run on the IMx ® analyzer available from Abbott Laboratories. Such an assay is illustrated more specifically in the examples which follow. A general description of microparticle capture enzyme immunoassays can be found in "*The Abbott IMx ® Automated Benchtop Immunochemistry Analyzer System*", by M. Fiore et al in *CLINICAL CHEMISTRY* Vol. 34, No. 9, 1726–1732 (1988) the disclosure of which is hereby incorporated by reference.

In general an analyte such as FK506 is determined in an MEIA by quantifying the rate of fluorescence development when a fluorogenic substrate is converted by the action of an enzyme-labeled conjugate. MEIAs as run on the IMx ® analyzer generally utilize a reagent pack containing microparticle reagent, an alkaline phosphatase conjugate, fluorogenic substrate and, optionally, a diluent buffer specific for the FK506 assay. Submicron microparticles coated with a capture molecule specific for FK506 being measured are used as the solid phase. Because the microparticles do not settle out of suspension during the course of the assay, they can be readily pipetted by the IMx ® instrument. The effective surface area of these polystyrene latex microparticles, which number in the millions, is several-fold greater than that of a $\frac{1}{4}$ inch diameter polystyrene bead commonly used in other commercial immunoassays. Because of this large surface area and the very small diffusion distance between analyte and the capture molecules on the surface of the microparticles, the capture phase of the MEIA typically reaches equilibrium within several minutes, allowing excellent throughput.

Unlike homogeneous fluorescent polarization immunoassays, the heterogeneous MEIA requires a separation step. After incubation of the microparticles with specimen, the microparticles are separated from the reaction mixture by transferring it to an inert glass fiber matrix in the MEIA reaction cell. This glass fiber surface provides a precisely located mechanical support for the microparticles during the subsequent optical read phase of the assay. The microparticles and bound analyte adhere strongly to the glass fibers, while the remaining specimen components are washed through the pores of the matrix to an underlying absorbent blotter. Detection of the immune complex on the glass fiber matrix is accomplished using an alkaline phosphatase-labeled conjugate. Conjugate is either incubated with the specimen and microparticles in a typical one step IMx ® MEIA or applied to the matrix after the initial wash step. It is contemplated that an MEIA for FK506 run on the IMx ® analyzer can be configured either in a "sandwich" or competitive assay format. In a sandwich configuration an alkaline phosphatase-anti-FK506 antibody conjugate is used, while an IMx ® competitive assay utilizes an FK-506-alkaline phosphatase conjugate.

In either configuration, the specifically bound alkaline phosphatase on the microparticles is detected by addition of a fluorogenic substrate, typically 4-methylumbelliferyl phosphate (4-MUP), to the matrix. The alkaline phosphatase catalyzes hydrolysis of the 4-MUP to inorganic phosphate and fluorescent 4-methylumbelliferone (4-MU). The liberated 4-MU is detected by the IMx ® MEIA optics assembly, a front surface fluorometer designed to detect fluorescence of low concentrations of 4-MU without interference by fluorescence of 4-MUP at 367 nanometers (nm). A system of lenses and optical filters focuses filtered light (365 nm wavelength) from a mercury arc lamp onto the surface of the matrix and focuses emitted fluorescence from 4-MU (448 nm wavelength) onto a photomultiplier tube. About 5% of the excitation light is detected by a photodiode, allowing normalization of the fluorescence data and generation of a control signal used by the lamp power supply to maintain the intensity of the excitation light within 5% over the useful life of the lamp. The instrument then uses linear regression analysis to convert the data from 8 successive determinations of 4-MU fluorescence to a rate, which rate is proportional to the concentration of alkaline phosphatase conjugate specifically bound to the microparticles, from which the concentration of FK506 in the sample can be determined.

The following examples are provided to further illustrate embodiments of the invention and should not be construed as a limitation on the scope of the invention.

EXAMPLE 1

This example illustrates the preparation of an aqueous composition of the invention utilizing whole human blood containing the anticoagulant, ethylenediamine tetraacetic acid (EDTA). It also illustrates a comparison of the stability of FK506 in the aqueous composition of the invention with the stability of FK506 in a synthetic blood matrix (prepared by adding hemoglobin to human serum) and with the stability of FK506 in plasma and serum A synthetic blood matrix was prepared by adding hemoglobin (10 grams/deciliter) to human serum. A stock standard of FK506 in methanol (10 micrograms FK506/ml) was spiked into this synthetic matrix to provide two initial concentrations of 32.2 nanograms FK506/ml (ng/ml)(high) and 7.5 ng/ml (low). A composition of the invention was prepared by adding the stock standard of FK506 in methanol (10 micrograms FK506/ml) into human whole blood (containing sufficient EDTA to prevent coagulation ) to provide two initial concentrations of 47.1 ng/ml (high) and 9.3 ng/ml (low). The stability of these two different matrices was evaluated by placing the four different standards at 37 degrees Celsius and determining the concentration of FK506 present as a function of time. The results, summarized in TABLE 1 below, illustrate that FK506 is much more stable in blood than in the synthetic matrix.

TABLE 1

| | Human Blood | | Synthetic Matrix | |
|---|---|---|---|---|
| Day | High (ng/ml) | Low (ng/ml) | High (ng/ml) | Low (ng/ml) |
| 0 | 47.1 | 9.3 | 32.2 | 7.5 |
| 1 | 41.7 | 8.5 | 24.9 | 5.0 |
| 2 | 51.1 | 12.8 | 11.6 | 0.4 |
| 7 | 46.1 | 9.6 | 3.0 | 3.5 |

Further evidence of the instability of FK506 in plasma and serum is shown below.

FK506 was spiked into plasma and serum and the stability at 37 degrees Celsius was evaluated as for human blood and the synthetic matrix above. The plasma contained sufficient EDTA as anti-coagulant to prevent coagulation.

Comparative plasma and serum matrices were prepared by adding a stock standard of FK506 in methanol (10 micrograms FK506/ml) to the plasma and serum matrices to provide two initial concentrations of 41.8 ng/ml (high) and 18.4 ng/ml (low) for the plasma and two initial concentrations of 44.9 ng/ml (high) and 22.4 ng/ml (low) for the serum. As for the human blood and synthetic matrix above, the stability of these two different matrices was evaluated by placing the four different standards at 37 degrees Celsius and determining the concentration of FK506 present as a function of time. The results, summarized in TABLE 2 below, illustrate that FK506 is also very unstable in plasma and serum compared to the stability of FK506 in a composition of the invention.

TABLE 2

| | Plasma | | Serum | |
|---|---|---|---|---|
| Day | High (ng/ml) | Low (ng/ml) | High (ng/ml) | Low (ng/ml) |
| 0 | 41.8 | 18.4 | 44.9 | 19.6 |
| 1 | 30.3 | 16.5 | 33.5 | 17.0 |
| 2 | 19.0 | 11.5 | 25.2 | 11.0 |
| 6 | 10.5 | 5.3 | 9.4 | 6.3 |

EXAMPLE 2

This example illustrates the utilization of blood cell fragments according to the invention to stabilize FK506 in an aqueous matrix. Human blood cells were lysed by sonication or by repetitive freeze-thaw cycles respectively. Lysis was judged complete by the absence of blood cells under microscopic examination. Except for the utilization of lysed human blood cells instead of whole blood cells, the FK506 standards were prepared in the same manner as in Example 1 above. As can be seen from the results summarized in TABLE 3 below, compared to the results summarized in TABLES 1 and 2 above, FK506 standards made in lysed blood were more stable at 45 degrees Celsius than FK506 standards in serum, plasma or synthetic blood at 37 degrees Celsius (see Example 1).

TABLE 3

| | Lysed Cells/Freeze-Thaw | | Lysed Cells/Sonication | |
|---|---|---|---|---|
| Day | High (ng/ml) | Low (ng/ml) | High (ng/ml) | Low (ng/ml) |
| 0 | 44.4 | 17.5 | 50.9 | 22.4 |
| 1 | 44.7 | 16.6 | 44.2 | 17.8 |
| 2 | 34.3 | 10.9 | 29.4 | 13.9 |
| 7 | 23.5 | 8.3 | 25.0 | 11.0 |

EXAMPLE 3

This example illustrates the utilization of human packed red blood cells (with EDTA as anticoagulant) and saline in an aqueous, FK506-containing composition of the invention. It also illustrates the enhanced stability of FK506 in this composition of the invention compared to the stability of FK506 in comparative serum and plasma compositions.

Human packed red blood cells (with sufficient EDTA added to prevent coagulation) were mixed in equal parts by volume with saline (0.9 percent by weight sodium chloride solution), human plasma or human serum. Three freeze-thaw cycles were done on each matrix combination to lyse the cells. The pH on each matrix was adjusted to pH 6.0 with 3 Molar (M) citric acid. FK506 standards were made in each matrix and stability at 45 degrees Celsius was evaluated as described above. While there were differences between the three matrices, FK506 was more stable in any of them relative to serum, plasma or synthetic blood matrices. Surprisingly, the most stable matrix was blood diluted with saline rather than with normal blood constituents found in plasma or serum.

TABLE 4

| | Saline | | Serum | | Plasma | |
|---|---|---|---|---|---|---|
| Day | High (ng/ml) | Low (ng/ml) | High (ng/ml) | Low (ng/ml) | High (ng/ml) | Low (ng/ml) |
| 0 | 62.2 | 24.8 | 65.0 | 26.4 | 67.8 | 26.3 |
| 1 | 60.5 | 25.4 | 42.9 | 21.7 | 57.4 | 23.1 |
| 2 | 51.3 | 22.4 | 31.0 | 14.5 | 46.9 | 20.0 |

TABLE 4-continued

| | Saline | | Serum | | Plasma | |
|---|---|---|---|---|---|---|
| Day | High (ng/ml) | Low (ng/ml) | High (ng/ml) | Low (ng/ml) | High (ng/ml) | Low (ng/ml) |
| 7 | 49.5 | 19.2 | 16.5 | 8.4 | 31.6 | 11.1 |

EXAMPLE 4

This example illustrates the suitability of non-human blood sources for a composition of the invention. In this example both sheep blood (non-lysed as in Example 1 above and containing the anti-coagulant citrate) and horse blood (lysed by freeze-thaw cycles as in Example 2 above and containing the anti-coagulant EDTA) were utilized. FK506 standards were made in each matrix and stability was evaluated at 37 degrees Celsius as described above. As can be seen from the results summarized in TABLE 5 below, both matrices showed excellent stability relative to aqueous matrices without blood components.

TABLE 5

| | Sheep | | Horse | |
|---|---|---|---|---|
| Day | High (ng/ml) | Low (ng/ml) | High (ng/ml) | Low (ng/ml) |
| 0 | 49.2 | 17.0 | 65.9 | 30.9 |
| 1 | 43.1 | 15.7 | 66.1 | 27.3 |
| 2 | 39.4 | 15.5 | 74.4 | 29.0 |
| 7 | 34.2 | 13.5 | 69.4 | 28.5 |

EXAMPLE 5

Whole blood has the undesirable characteristic of thickening at elevated temperatures. Thickened blood can be difficult or impossible to pipet which can make a blood matrix completely unsuitable as a standard for a diagnostic assay. The thickening of blood can be reduced in a composition of the invention by dilution with saline (0.9 percent by weight sodium chloride solution) and as indicated in Example 3 above, one would expect FK506 standards made in the resulting matrix to show good stability.

Whole blood (plus sufficient EDTA to prevent coagulation) was lysed by freeze-thaw cycles and diluted with saline so as to be at final saline concentrations of 10, 20 and 30 percent by volume. FK506 in methanol was spiked into the matrix to make standards and the stability was evaluated at 37 degrees Celsius as described above. As the results summarized in the following TABLE 6 indicate, the standards made in the diluted matrices showed good stability.

TABLE 6

| | FK506 (ng/ml) | | |
|---|---|---|---|
| Day | 10% Saline | 20% Saline | 30% Saline |
| 0 | 73.7 | 72.4 | 74.1 |
| 1 | 75.7 | 76.4 | 81.4 |
| 2 | 73.2 | 72.3 | 71.9 |
| 8 | 64.2 | 57.8 | 65.2 |

EXAMPLE 6

This example illustrates the preparation of Microparticle Reagent for utilization in an assay utilizing a composition of the invention.

A monoclonal antibody directed against FK506 (Fujisawa clone #1-60-46) was covalently coupled to carboxylate modified latex microparticles (0.392 microns) by established procedures. These methods are extensively reviewed in Uniform Latex Particles (1987) L. B. Bangs, Seragen Diagnostics, Inc. In brief, final concentrations of antibody (1.2 mg/ml), microparticles (0.6% solids) and EDAC (1-ethyl-3-(3-dimethylaminopropyl)carbodiimide hydrochloride) (0.42 μM) are mixed, the pH adjusted to 5.7 and the reaction allowed to proceed for 12–18 hours at 2–8 degrees Celsius. The microparticles are then washed by repetitive centrifugation and resuspension cycles and the microparticles are diluted to the final working concentration.

EXAMPLE 7

This example illustrates the preparation of FK506-hemisuccinate and its active ester for utilization in the preparation of the alkaline phosphatase conjugate of Example 8.

FK506 (250 mg) was dissolved in pyridine (7 ml). To the solution were added succinic anhydride (145 mg) and 4 dimethylaminopyridine (7 mg). The mixture was stirred at room temperature for about 72 hours. The reaction mixture was concentrated to dryness under reduced pressure and the residue was subjected to silica gel column chromatography. Development with a mixture of 10 percent by volume methanol and 90 percent by volume methylene chloride gave 86.8 mg of the hemisuccinate The FK506 hemisuccinate (35 mg), N-hydroxysuccinimide (5.4 mg) and N,N'-dicyclohexylcarbodiimide (8.8 mg/ml) were dissolved in 5 ml ethyl acetate and stirred for 24 hours at room temperature. The reaction mixture was filtered and dried to give 44.1 mg of a mixture containing the active ester and N,N'-dicyclohexylurea. The material was used without further purification.

EXAMPLE 8

This example illustrates the preparation of the FK506-Alkaline Phosphate Conjugate Reagent.

One milligram (1 mg) of the active ester described above was solubilized in 0.5 ml of dimethylformamide (DMF). An amount of 0.14 ml of this solution was mixed with 0.62 ml of DMF and added to 10 ml of calf intestine alkaline phosphatase (10 mg). The solution was mixed for 2.5 hours at room temperature and then 1 ml of 1.8M Tris was added. This solution was dialyzed against buffer (0.1M NaCl, 2 mM $MgCl_2$, 0.1 mM $ZnCl_2$, 0.1% $NaN_3$, 0.05M Tris-HCl, pH=7.5) at 2–8 degrees Celsius and then bovine serum albumin was added to a final concentration of 1%. This stock solution of FK506-alkaline phosphatase conjugate was diluted to the working concentrations as necessary.

EXAMPLE 9

This example illustrates the preparation of Precipitation Reagent.

The whole blood precipitation reagent was prepared with final concentrations of 60 mM $ZnSO_4$, 50% weight/volume (w/v) methanol and 30% ethylene glycol.

EXAMPLE 10

This example illustrates the preparation of Blood FK506 Standards.

Human whole blood was lyzed by three freeze-thaw cycles and the pH of the blood adjusted to pH 6.0 by the addition of 3M citric acid. FK506 in methanol (10 micrograms/ml) was spiked into this matrix so as to make standards containing 10, 20, 30, 50 and 80 nanograms/ml of FK506. An additional standard was prepared in the same way except for the addition of FK506 in methanol, thus providing a standard containing 0 nanograms/ml of FK506.

EXAMPLE 11

The whole blood solutions containing 0, 10, 20, 30, 50 and 80 nanograms/ml FK506 (of Example 10 above) were each tested following the assay protocol described below. One hundred (100) microliters of sample was added to 200 microliters of precipitation reagent and the mixture vortexed for 5-10 seconds. The precipitates formed were pelleted by centrifugation and the clear supernatant decanted into the sample well of an IMx® sample cartridge. Forty (40) microliters of this organic sample was added directly to 50 microliters of the microparticle reagent and 160 microliters of IMx® dilution buffer. The reaction mixture was incubated at 33-36 degrees Celsius for 10 minutes and then 175 microliters of this mixture was transferred onto a glass fiber filter. The filter was washed with IMx® dilution buffer and then 40 microliters of the FK506-alkaline phosphatase conjugate reagent was added to the filter. Following a second wash step, 50 microliters of alkaline phosphatase substrate, 4-methylumbelliferyl phosphate, was added to the filter. Conjugate bound to the filter converted the substrate to a fluorescent product which was quantified by front surface fluorescence measurements. The rate of production of the product was directly proportional to the amount of conjugate bound and thus indirectly proportional to the amount of FK506 bound to the microparticles. The measurements were as set forth in the following TABLE 7.

TABLE 7

| Concentration FK506 (ng/ml) | Fluorescent Rate |
| --- | --- |
| 0 | 416 |
| 10 | 288 |
| 20 | 197 |
| 30 | 150 |
| 50 | 111 |
| 80 | 79 |

The measurements obtained show that by employing the subject method a standard curve can be made to analyze whole blood containing unknown FK506 concentrations.

What is claimed is:

1. An in vitro aqueous composition suitable as a standard for a diagnostic assay for FK506 comprising:
   (1) FK506;
   (2) whole blood cells which have not been fixed;
   (3) water; and
   (4) an organic solvent compatible with FK506 and the whole blood cells at a concentration of less than 10% weight/volume; wherein said whole blood cells are present in an amount sufficient to enhance the stability of FK506 in said composition over the stability of FK506 in said composition without the presence of said whole blood cells for at least one day at 37° C.

2. The aqueous composition of claim 1 having a hematocrit, based on whole blood cells, of less than 40 percent by volume of said composition.

3. The aqueous composition of claim 1 additionally comprising: (5) an alkali halide selected from the group consisting of potassium chloride and sodium chloride.

4. The aqueous composition of claim 1 having a pH of between about 7.0 and about 4.0.

5. The aqueous composition of claim 1 having less than 1.0 percent weight/volume of said organic solvent.

6. The aqueous composition of claim 1 having from 5 to 70 nanograms FK506/milliliter based on the total volume of said composition.

7. The aqueous composition of claim 3 prepared from 90 to 20 percent by volume whole blood and from 10 to 80 percent by volume of aqueous alkali halide solution having an alkali halide concentration of 0.9 percent by weight.

8. The aqueous composition of claim 4 wherein said alkali halide is sodium chloride.

9. The aqueous composition of claim 3 having a hematocrit, based on whole blood cells, of less than 40 percent by volume of said composition; having from 5 to 70 nanograms FK506/milliliter based on the total volume of said composition; having less than 1.0 percent weight/volume of said organic solvent; having a pH of from 6.0 to 6.5; and prepared from 90 to 80 percent by volume of whole blood and from 10 to 20 percent by volume of aqueous alkali halide solution having a salt concentration of 0.9 percent by weight.

10. The aqueous composition of claim 1 which is isotonic at 20 degrees Celsius and 1 atmosphere pressure.

11. An in vitro aqueous composition suitable as a standard for a diagnostic assay for FK506 comprising:
   (1) FK506;
   (2) a whole blood component consisting essentially of whole blood cells having been lysed to as to be essentially free of microscopically visible blood cells;
   (3) water; and
   (4) an organic solvent compatible with FK506 and the whole blood component at a concentration of less than 10% weight/volume; wherein said whole blood component is present in an amount sufficient to enhance the stability of FK506 in said composition over the stability of FK506 in said composition without the presence of said whole blood component at room temperature and atmospheric pressure.

12. The aqueous composition of claim 11 having a hematocrit, based on whole blood cells prior to lysing, of less than 40 percent by volume of said composition.

13. The aqueous composition of claim 11 additionally comprising: (5) an alkali halide selected from the group consisting of potassium chloride and sodium chloride.

14. The aqueous composition of claim 11 having a pH of between about 7.0 and about 4.0.

15. The aqueous composition of claim 11 having less than 1.0 percent weight/volume of said organic solvent.

16. The aqueous composition of claim 11 having from 5 to 70 nanograms FK506/milliliter based on the total volume of said composition.

17. The aqueous composition of claim 13 prepared from 90 to 20 percent by volume whole blood and from 10 to 80 percent by volume of aqueous alkali halide solution having an alkali halide concentration of 0.9 percent by weight.

18. The aqueous composition of claim 17 wherein said alkali halide is sodium chloride.

19. The aqueous composition of claim 13 having a hematocrit, based on whole blood cells, of less than 40 percent by volume of said composition; having from 5 to 70 nanograms FK506/milliliter based on the total volume of said composition; having less than 1.0 percent weight/volume of said organic solvent; having a pH of from 6.0 to 6.5; and prepared from 90 to 80 percent by volume of whole blood and from 10 to 20 percent by volume of aqueous alkali halide solution having a salt concentration of 0.9 percent by weight.

20. A diagnostic assay for the determination of FK506 in a sample of biological fluid comprising a step of generating a standard curve using as standards x aqueous compositions wherein x is an integer greater than one, each of said x aqueous compositions comprising:
   (1) FK506;
   (2) whole blood cells which have not been fixed;
   (3) water; and
   (4) an organic solvent compatible with FK506 and the whole blood cells at a concentration of less than 10% weight/volume;
   said whole blood cells are present in each of said aqueous compositions in an amount sufficient to enhance the stability of FK506 in each said aqueous composition over the stability of FK506 in each said aqueous composition without the presence of said whole blood cells for at least one day at 37° C., and each of said aqueous compositions contains a different amount of FK506.

21. A diagnostic assay for determination of FK506 in a sample of biological fluid comprising a step of generating a standard curve using as standards x aqueous compositions wherein x is an integer greater than one, each of said x aqueous compositions comprising:
   (1) FK506;
   (2) a whole blood component consisting essentially of whole blood cells which have been lysed;
   (3) water; and
   (4) an organic solvent compatible with FK506 and the whole blood component at a concentration of less than 10% weight/volume.
   said whole blood component is present in each of said aqueous compositions in an amount sufficient to enhance the stability of FK506 in each said aqueous composition over the stability of FK506 in each said aqueous composition without the presence of said whole blood component for at least one day at 37° C. and each of said aqueous compositions contains a different amount of FK506.

* * * * *